US007745151B2

(12) United States Patent
He et al.

(10) Patent No.: US 7,745,151 B2
(45) Date of Patent: Jun. 29, 2010

(54) METHODS OF DETERMINING BINDING BETWEEN NOGO RECEPTOR AND P75 NEUROTROPHIN RECEPTOR

(75) Inventors: Zhigang He, Boston, MA (US); Kevin C. Wang, Boston, MA (US); Jieun A. Kim, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 979 days.

(21) Appl. No.: 10/211,157

(22) Filed: Aug. 2, 2002

(65) Prior Publication Data

US 2004/0029169 A1 Feb. 12, 2004

(51) Int. Cl.
*G01N 33/567* (2006.01)

(52) U.S. Cl. ...................................................... 435/7.2

(58) Field of Classification Search ....................... None
See application file for complete search history.

(56) References Cited

FOREIGN PATENT DOCUMENTS

WO WO 03031462 A2 * 4/2003

OTHER PUBLICATIONS

Wang et al (2002). Nature. 420, 74-78.*

Jung et al. Regulated intramembrane proteolysis of the p75 neurotrophin receptor modulates its association with the TrkA receptor. J Biol Chem. Oct. 24, 2003;278(43):42161-9. Epub Aug. 11, 2003.*

* cited by examiner

*Primary Examiner*—Daniel E. Kolker
*Assistant Examiner*—Gregory S Emch
(74) *Attorney, Agent, or Firm*—Richard Aron Osman

(57) ABSTRACT

Inhibitors of Nogo Receptor (NgR)-p75 binding are used to reduce NgR-p75 binding mediated axon growth inhibition. Mixtures of NgR and p75 are used in pharmaceutical screens to characterize agents as inhibiting binding of NgR to p75 and promoting axon regeneration.

21 Claims, No Drawings

SEQUENCE LISTING

```
<160> NUMBER OF SEQ ID NOS: 12

<210> SEQ ID NO 1
<211> LENGTH: 136
<212> TYPE: PRT
<213> ORGANISM: human

<400> SEQUENCE: 1

Ala Val Ala Thr Gly Pro Tyr His Pro Ile Trp Thr Gly Arg Ala Thr
  1               5                  10                  15

Asp Glu Glu Pro Leu Gly Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Gly Arg Val Pro Pro Gly Asp Ser Pro Pro Gly Asn Gly
     50                  55                  60

Ser Gly Pro Arg His Ile Asn Asp Ser Pro Phe Gly Thr Leu Pro Gly
 65                  70                  75                  80

Ser Ala Glu Pro Pro Leu Thr Ala Val Arg Pro Glu Gly Ser Glu Pro
                 85                  90                  95

Pro Gly Phe Pro Thr Ser Gly Pro Arg Arg Arg Pro Gly Cys Ser Arg
            100                 105                 110

Lys Asn Arg Thr Arg Ser His Cys Arg Leu Gly Gln Ala Gly Ser Gly
        115                 120                 125

Gly Gly Gly Thr Gly Asp Ser Glu
    130                 135
```

```
<210> SEQ ID NO 2
<211> LENGTH: 136
<212> TYPE: PRT
<213> ORGANISM: mouse

<400> SEQUENCE: 2

Ala Val Ala Ser Gly Pro Phe Arg Pro Ile Gln Thr Ser Gln Leu Thr
  1               5                  10                  15

Asp Glu Glu Leu Leu Ser Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Gly Arg Val Pro Pro Gly Asp Thr Pro Pro Gly Asn Gly
     50                  55                  60

Ser Gly Pro Arg His Ile Asn Asp Ser Pro Phe Gly Thr Leu Pro Ser
 65                  70                  75                  80

Ser Ala Glu Pro Pro Leu Thr Ala Leu Arg Pro Gly Gly Ser Glu Pro
                 85                  90                  95

Pro Gly Leu Pro Thr Thr Gly Pro Arg Arg Arg Pro Gly Cys Ser Arg
            100                 105                 110

Lys Asn Arg Thr Arg Ser His Cys Arg Leu Gly Gln Ala Gly Ser Gly
        115                 120                 125

Ala Ser Gly Thr Gly Asp Ala Glu
    130                 135


<210> SEQ ID NO 3
<211> LENGTH: 136
<212> TYPE: PRT
<213> ORGANISM: rat

<400> SEQUENCE: 3

Ala Val Ala Ser Gly Pro Phe Arg Pro Ile Gln Thr Ser Gln Leu Thr
  1               5                  10                  15

Asp Glu Glu Leu Leu Ser Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Gly Arg Val Pro Pro Gly Asp Thr Pro Pro Gly Asn Gly
     50                  55                  60

Ser Gly Pro Arg His Ile Asn Asp Ser Pro Phe Gly Thr Leu Pro Ser
 65                  70                  75                  80

Ser Ala Glu Pro Pro Leu Thr Ala Leu Arg Pro Gly Gly Ser Glu Pro
                 85                  90                  95

Pro Gly Leu Pro Thr Thr Gly Pro Arg Arg Arg Pro Gly Cys Ser Arg
            100                 105                 110

Lys Asn Arg Thr Arg Ser His Cys Arg Leu Gly Gln Ala Gly Ser Gly
        115                 120                 125

Ala Ser Gly Thr Gly Asp Ala Glu
    130                 135


<210> SEQ ID NO 4
<211> LENGTH: 136
<212> TYPE: PRT
<213> ORGANISM: Artificial Sequence
<220> FEATURE:
<223> OTHER INFORMATION: Description of Artificial Sequence: Synthetic
      Peptide Sequence
```

-continued

<400> SEQUENCE: 4

```
Ala Val Ala Thr Gly Pro Tyr His Pro Ile Trp Thr Gly Arg Ala Thr
  1               5                  10                  15

Asp Glu Glu Pro Leu Gly Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Gly Arg Val Pro Pro Gly Asp Ser Pro Pro Ala Asn Gly
     50                  55                  60

Ser Gly Pro Arg His Val Asn Asp Ser Pro Phe Gly Thr Leu Pro Gly
 65                  70                  75                  80

Ser Ala Glu Pro Pro Leu Thr Ala Ile Arg Pro Glu Gly Ser Glu Pro
                 85                  90                  95

Pro Gly Phe Pro Thr Ser Gly Pro Arg Arg Arg Pro Gly Cys Ser Arg
            100                 105                 110

Lys Asn Arg Thr Arg Ser His Cys Arg Leu Gly Gln Ala Gly Ser Gly
        115                 120                 125

Gly Gly Gly Thr Gly Asp Ser Glu
    130                 135
```

<210> SEQ ID NO 5
<211> LENGTH: 136
<212> TYPE: PRT
<213> ORGANISM: Artificial Sequence
<220> FEATURE:
<223> OTHER INFORMATION: Description of Artificial Sequence: Synthetic Peptide Sequence

<400> SEQUENCE: 5

```
Ala Val Ala Ser Gly Pro Phe Arg Pro Ile Gln Thr Ser Gln Leu Thr
  1               5                  10                  15

Asp Glu Glu Leu Leu Ser Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Gly Arg Val Pro Pro Gly Asp Thr Pro Pro Gly Asn Gly
     50                  55                  60

Ser Gly Pro Arg His Ile Asn Asp Ser Pro Phe Gly Thr Leu Pro Ser
 65                  70                  75                  80

Ser Ala Glu Pro Pro Leu Thr Ala Leu Arg Pro Gly Gly Ser Glu Pro
                 85                  90                  95

Pro Gly Leu Pro Thr Thr Gly Pro Arg Arg Arg Pro Gly Cys Ser Arg
            100                 105                 110

Lys Asn Arg Thr Arg Thr His Cys Arg Val Gly Gln Ala Gly Ser Gly
        115                 120                 125

Ala Ser Ala Thr Gly Asp Ala Glu
    130                 135
```

<210> SEQ ID NO 6
<211> LENGTH: 136
<212> TYPE: PRT
<213> ORGANISM: Artificial Sequence
<220> FEATURE:
<223> OTHER INFORMATION: Description of Artificial Sequence: Synthetic Peptide Sequence

<400> SEQUENCE: 6

-continued

```
Ala Val Ala Ser Ala Pro Phe Arg Pro Ile Gln Thr Ser Gln Leu Thr
  1               5                  10                  15

Asp Glu Glu Ala Ala Ser Leu Pro Lys Cys Cys Gln Pro Asp Ala Ala
             20                  25                  30

Asp Lys Ala Ser Val Leu Glu Pro Gly Arg Pro Ala Ser Ala Gly Asn
         35                  40                  45

Ala Leu Lys Ala Arg Val Pro Pro Gly Asp Thr Pro Pro Gly Asn Gly
     50                  55                  60

Ser Gly Pro Arg His Ile Asn Asp Ser Pro Phe Gly Thr Leu Pro Ser
 65                  70                  75                  80

Ser Ala Glu Pro Pro Leu Thr Ala Leu Arg Pro Gly Gly Ser Glu Pro
                 85                  90                  95

Pro Gly Leu Pro Thr Thr Gly Pro Arg Arg Arg Pro Gly Cys Ser Arg
            100                 105                 110

Lys Asn Arg Thr Arg Ser His Cys Arg Leu Gly Gln Ala Gly Ser Gly
        115                 120                 125

Ala Ser Gly Thr Gly Asp Ala Glu
    130                 135
```

<210> SEQ ID NO 7
<211> LENGTH: 250
<212> TYPE: PRT
<213> ORGANISM: human

<400> SEQUENCE: 7

```
Met Gly Ala Gly Ala Thr Gly Arg Ala Met Asp Gly Pro Arg Leu Leu
  1               5                  10                  15

Leu Leu Leu Leu Leu Gly Val Ser Leu Gly Gly Ala Lys Glu Ala Cys
             20                  25                  30

Pro Thr Gly Leu Tyr Thr His Ser Gly Glu Cys Cys Lys Ala Cys Asn
         35                  40                  45

Leu Gly Glu Gly Val Ala Gln Pro Cys Gly Ala Asn Gln Thr Val Cys
     50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
                 85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240
```

```
Pro Val Val Thr Arg Gly Thr Thr Asp Asn
                245                 250


<210> SEQ ID NO 8
<211> LENGTH: 251
<212> TYPE: PRT
<213> ORGANISM: rat

<400> SEQUENCE: 8

Met Arg Arg Ala Gly Ala Ala Cys Ser Ala Met Asp Arg Leu Arg Leu
  1               5                  10                  15

Leu Leu Leu Leu Ile Leu Gly Val Ser Ser Gly Gly Ala Lys Glu Thr
             20                  25                  30

Cys Ser Thr Gly Leu Tyr Thr His Ser Gly Glu Cys Cys Lys Ala Cys
         35                  40                  45

Asn Leu Gly Glu Gly Val Ala Gln Pro Cys Gly Ala Asn Gln Thr Val
     50                  55                  60

Cys Glu Pro Cys Leu Asp Asn Val Thr Phe Ser Asp Val Val Ser Ala
 65                  70                  75                  80

Thr Glu Pro Cys Lys Pro Cys Thr Glu Cys Leu Gly Leu Gln Ser Met
                 85                  90                  95

Ser Ala Pro Cys Val Glu Ala Asp Asp Ala Val Cys Arg Cys Ala Tyr
            100                 105                 110

Gly Tyr Tyr Gln Asp Glu Glu Thr Gly His Cys Glu Ala Cys Ser Val
        115                 120                 125

Cys Glu Val Gly Ser Gly Leu Val Phe Ser Cys Gln Asp Lys Gln Asn
    130                 135                 140

Thr Val Cys Glu Glu Cys Pro Glu Gly Thr Tyr Ser Asp Glu Ala Asn
145                 150                 155                 160

His Val Asp Pro Cys Leu Pro Cys Thr Val Cys Glu Asp Thr Glu Arg
                165                 170                 175

Gln Leu Arg Glu Cys Thr Pro Trp Ala Asp Ala Glu Cys Glu Glu Ile
            180                 185                 190

Pro Gly Arg Trp Ile Pro Arg Ser Thr Pro Pro Glu Gly Ser Asp Ser
        195                 200                 205

Thr Ala Pro Ser Thr Gln Glu Pro Glu Val Pro Pro Glu Gln Asp Leu
    210                 215                 220

Val Pro Ser Thr Val Ala Asp Met Val Thr Thr Val Met Gly Ser Ser
225                 230                 235                 240

Gln Pro Val Val Thr Arg Gly Thr Thr Asp Asn
                245                 250


<210> SEQ ID NO 9
<211> LENGTH: 243
<212> TYPE: PRT
<213> ORGANISM: mouse

<400> SEQUENCE: 9

Met Asp Arg Leu Arg Leu Leu Leu Leu Leu Leu Leu Leu Leu Gly Val
  1               5                  10                  15

Ser Phe Gly Gly Ala Lys Glu Thr Cys Ser Thr Gly Met Tyr Thr His
             20                  25                  30

Ser Gly Glu Cys Cys Lys Ala Cys Asn Leu Gly Glu Gly Val Ala Gln
         35                  40                  45

Pro Cys Gly Ala Asn Gln Thr Val Cys Glu Pro Cys Leu Asp Ser Val
     50                  55                  60
```

-continued

```
Thr Phe Ser Asp Val Val Ser Ala Thr Glu Pro Cys Lys Pro Cys Thr
 65                  70                  75                  80

Glu Cys Leu Gly Leu Gln Ser Met Ser Ala Pro Cys Val Glu Ala Asp
                 85                  90                  95

Asp Ala Val Cys Arg Cys Ser Tyr Gly Tyr Tyr Gln Asp Glu Glu Thr
            100                 105                 110

Gly Arg Cys Glu Ala Cys Ser Val Cys Gly Val Gly Ser Gly Leu Val
        115                 120                 125

Phe Ser Cys Gln Asp Lys Gln Asn Thr Val Cys Glu Glu Cys Pro Glu
    130                 135                 140

Gly Thr Tyr Ser Asp Glu Ala Asn His Val Asp Pro Cys Leu Pro Cys
145                 150                 155                 160

Thr Val Cys Glu Asp Thr Glu Arg Gln Leu Arg Glu Cys Thr Pro Trp
                165                 170                 175

Ala Asp Ala Glu Cys Glu Glu Ile Pro Gly Arg Trp Ile Thr Arg Ser
            180                 185                 190

Thr Pro Pro Glu Gly Ser Asp Val Thr Thr Pro Ser Thr Gln Glu Pro
        195                 200                 205

Glu Ala Pro Pro Glu Arg Asp Leu Ile Ala Ser Thr Val Ala Asp Thr
    210                 215                 220

Val Thr Thr Val Met Gly Ser Ser Gln Pro Val Val Thr Arg Gly Thr
225                 230                 235                 240

Ala Asp Asn


<210> SEQ ID NO 10
<211> LENGTH: 250
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 10

Met Gly Ala Gly Ala Thr Gly Arg Ala Met Asp Gly Pro Arg Leu Leu
  1               5                  10                  15

Leu Leu Leu Leu Leu Gly Leu Ser Val Gly Gly Ala Lys Glu Ala Cys
             20                  25                  30

Pro Thr Gly Leu Tyr Thr His Ser Gly Glu Cys Cys Lys Ala Cys Asn
         35                  40                  45

Leu Gly Glu Gly Val Ala Gln Pro Cys Gly Ala Asn Gln Thr Val Cys
     50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
                 85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Ser
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175
```

-continued

```
Leu Arg Glu Cys Thr Arg Trp Ala Asp Ala Glu Cys Glu Glu Val Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Ile Ile Thr Arg Gly Thr Thr Asp Lys
                245                 250


<210> SEQ ID NO 11
<211> LENGTH: 250
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 11

Met Arg Arg Ala Gly Ala Ala Cys Ser Ala Met Asp Arg Leu Arg Leu
  1               5                  10                  15

Leu Leu Leu Leu Ile Leu Gly Val Ser Ser Gly Gly Ala Lys Glu Thr
            20                  25                  30

Cys Ser Thr Gly Leu Tyr Thr His Ser Gly Glu Cys Cys Lys Ala Cys
        35                  40                  45

Asn Leu Gly Glu Gly Val Ala Gln Pro Cys Gly Ala Asn Gln Thr Val
     50                  55                  60

Cys Glu Pro Cys Leu Asp Asn Val Thr Phe Ser Asp Val Val Ser Ala
 65                  70                  75                  80

Thr Glu Pro Cys Lys Pro Cys Thr Glu Cys Leu Gly Leu Gln Ser Met
                85                  90                  95

Ser Ala Pro Cys Val Glu Ala Asp Asp Ala Val Cys Arg Cys Ala Tyr
            100                 105                 110

Gly Tyr Tyr Gln Asp Glu Glu Thr Gly His Cys Glu Ala Cys Ser Val
        115                 120                 125

Cys Glu Val Gly Ser Gly Leu Ile Phe Ser Cys Gln Asp Lys Gln Asn
    130                 135                 140

Thr Val Cys Glu Glu Cys Pro Glu Gly Thr Tyr Ser Asp Glu Ala Asn
145                 150                 155                 160

His Val Asp Pro Cys Val Pro Cys Thr Leu Cys Glu Asp Thr Glu Arg
                165                 170                 175

Gln Leu Arg Glu Cys Thr Pro Trp Ala Asp Ala Glu Cys Glu Glu Ile
            180                 185                 190

Pro Gly Arg Trp Val Pro Arg Ser Thr Pro Pro Glu Gly Ser Asp Ser
        195                 200                 205

Thr Ala Pro Ser Thr Gln Glu Pro Glu Val Pro Pro Glu Gln Asp Val
    210                 215                 220

Leu Pro Ser Thr Val Ala Asp Met Val Thr Thr Val Met Gly Ser Ser
225                 230                 235                 240

Gln Pro Val Val Thr Arg Gly Thr Thr Asn
                245                 250


<210> SEQ ID NO 12
<211> LENGTH: 243
<212> TYPE: PRT
```

-continued

```
<213> ORGANISM: Artificial Sequence
<220> FEATURE:
<223> OTHER INFORMATION: Description of Artificial Sequence: Synthetic
      peptide sequence

<400> SEQUENCE: 12

Met Asp Arg Leu Arg Leu Leu Leu Leu Leu Leu Leu Leu Leu Gly Val
  1               5                  10                  15

Ser Phe Gly Gly Ala Lys Glu Thr Cys Ser Thr Gly Met Tyr Thr His
             20                  25                  30

Ser Gly Glu Cys Cys Lys Ala Cys Asn Leu Gly Glu Gly Val Ala Gln
         35                  40                  45

Pro Cys Gly Ala Asn Gln Thr Val Cys Glu Pro Cys Leu Asp Ser Val
     50                  55                  60

Thr Phe Ser Asp Val Val Ser Ala Thr Glu Pro Cys Lys Pro Cys Thr
 65                  70                  75                  80

Ala Cys Leu Gly Leu Gln Ser Met Ser Ala Pro Cys Val Glu Ala Asp
                 85                  90                  95

Asp Ala Val Cys Arg Cys Ser Tyr Gly Tyr Tyr Gln Asp Glu Glu Thr
            100                 105                 110

Gly Arg Cys Glu Ala Cys Ser Val Cys Gly Ile Gly Ser Gly Leu Val
        115                 120                 125

Phe Ser Cys Gln Asp Lys Gln Asn Thr Val Cys Glu Glu Cys Pro Glu
    130                 135                 140

Gly Thr Tyr Ser Asp Glu Ala Asn His Val Asp Pro Cys Leu Pro Cys
145                 150                 155                 160

Thr Val Cys Glu Asp Thr Glu Arg Gln Leu Arg Glu Cys Thr Pro Trp
                165                 170                 175

Ala Asp Ala Glu Cys Glu Glu Ile Pro Gly Arg Trp Ile Thr Arg Ser
            180                 185                 190

Thr Pro Pro Glu Gly Ser Asp Val Thr Thr Pro Ser Thr Gln Glu Pro
        195                 200                 205

Glu Ala Pro Pro Glu Arg Glu Leu Ile Ala Ser Thr Val Ala Asp Thr
    210                 215                 220

Val Thr Thr Val Met Gly Ser Ser Gln Pro Val Val Thr Arg Gly Thr
225                 230                 235                 240

Ala Glu Gln
```

METHODS OF DETERMINING BINDING BETWEEN NOGO RECEPTOR AND P75 NEUROTROPHIN RECEPTOR

This work supported by NIH Federal Grant Nos. DA15335 and NS41999. The government may have certain rights in any patent issuing on this application.

INTRODUCTION

1. Field of the Invention

The invention is in the field of reducing myelin-mediated inhibition of axon regeneration.

2. Background of the Invention

The neurotrophin receptor $p75^{NTR}$ (p75) is a membrane glycoprotein that binds all known neurotrophins and has been reported to correlate with and promote axon outgrowth (Yamashita et al. 1999, Neuron 24, 585-93; Dechant, et al. Curr Opin Neurobiol 7, 413-418, 1997; Hempstead et al. Curr. Opin. Neurobiol. 12, 260-267, 2002). More recently, Yamashita et al. (May 13, 2002, J Cell Biol 157, 565-570, p. 568, col 1) report that p75 also binds ganglioside GT1b, forming a receptor complex which binds myelin-associated glycoprotein (MAG), and suggest a dual signaling role for p75 wherein neurotrophin binding promotes axonal outgrowth by inhibiting RhoA, and MAG binding inhibits growth by activating RhoA activity (supra, at p. 568, col. 2).

Unfortunately, general targeting of p75 or MAG have not proven viable strategies for promoting axon regeneration. In fact, Yamashita et al. (1999, supra) found that in vivo, axonal outgrowth is inhibited by p75 gene disruption. Furthermore, in vivo, axonal outgrowth appears unaffected by MAG gene disruption (Domeniconi et al., 2002, Neuron 35, 283-290, 287, col. 2; published online Jun. 28, 2002. DOI: 10.1016/S0896627302007705). In fact, MAG appears to be a relatively minor contributor to myelin-mediated growth inhibition, compared with p75 and NogoA (see, Wang et al. Nature 417(6892):941-944, Supplementary Information), and may be physiologically redundant to these more potent inhibitors (Domeniconi et al. 2002, supra, 287-288).

In contrast to the p75-GT1b binding of Yamashita et al. (2002, supra), the present inventors have found that p75 complexes with the Nogo receptor (NgR) and through NgR mediates inhibitory signaling of the major myelin-derived inhibitors, p75 and NogoA. Based on this finding, the inventors developed and disclose here methods for assaying NgR-p75 binding, including NgR-p75-mediated signaling, which methods are used to screen for specific inhibitors of NgR-p75 binding. In addition, the invention provides specific inhibitors of NgR-p75 binding and signal transduction, including NgR- and p75-derived peptides, and NgR and p75-specific antibodies, and their use in promoting outgrowth of CNS neurons in vivo.

SUMMARY OF THE INVENTION

The invention provides methods and compositions for assaying NgR-p75 binding and reducing axon growth inhibition mediated by NgR-p75 binding. The subject assays comprise the steps of (a) providing a mixture comprising a p75-binding domain of NgR and an NgR-binding domain of p75; and (b) measuring binding of the NgR domain to the p75 domain. In particular embodiments of the assay, one of the NgR domain and the p75 domain is soluble; one of the domains is soluble and the other is membrane-bound; one of the domains is recombinantly expressed on the surface of a cell, particularly a neuron; and/or the mixture is cell-free. In a particular embodiment, the mixture further comprises an inhibitor of NgR-p75 binding, wherein but for the presence of the inhibitor, the mixture provides a control binding of the NgR domain to the p75 domain; and the measuring step measures an inhibitor-biased binding of the domains lower than the control binding.

In another embodiment, the invention provides a method for characterizing an agent as modulating NgR-p75 binding, the method comprising the steps of (a) incubating a mixture comprising a p75-binding NgR domain, an NgR-binding p75 domain and an agent under conditions whereby but for the presence of the agent, the NgR domain and the p75 domain exhibit a control binding; and (b) detecting a resultant modulated domain binding different from the control binding as an indication that the agent modulates NgR-p75 binding.

The invention also provides compositions and mixtures specifically tailored for practicing the subject methods. For example, the invention provides specific inhibitors of NgR-p75 binding, including (a) inhibitors identified according to the method of claim 1, wherein the mixture further comprises an inhibitor of NgR-p75 binding, wherein but for the presence of the inhibitor, the mixture provides a control binding of the NgR domain to the p75 domain, and the measuring step measures an inhibitor-biased binding of the domains lower than the control binding and (b) inhibitors such as an NgR peptide which specifically inhibits NgR-p75 binding and does not inhibit NgR binding to MAG, oligodendrocyte myelin glycoprotein (OMgp) and NogoA; a p75 peptide which specifically inhibits NgR-p75 binding and does not inhibit p75 binding to NGF and GT1b; an NgR peptide-specific antibody fragment which specifically inhibits NgR-p75 binding and does not inhibit NgR binding to MAG, OMgp and NogoA; and a p75 peptide-specific antibody fragment which specifically inhibits NgR-p75 binding and does not inhibit p75 binding to NGF and GT1b.

The invention also provides methods for reducing axon growth inhibition mediated by NgR-p75 binding and detecting resultant reduced axon growth inhibition, the method comprising steps of (a) contacting a mixture comprising an axon subject to NgR-p75 binding mediated growth inhibition with a specific inhibitor of said NgR-p75 binding, under conditions wherein the inhibitor reduces said NgR-p75 binding mediated growth inhibition, and (b) detecting a resultant reduced axon growth inhibition. The axon may be in vitro, or in situ, and the method may be practiced in a variety of particular embodiments, such as (a) the inhibitor is a candidate inhibitor not previously characterized to bind NgR or p75, nor to inhibit NgR-p75 binding, nor to reduce axon growth inhibition mediated by NgR-p75 binding, and the detecting step characterizes the candidate agent as reducing axon growth inhibition mediated by NgR-p75 binding; (b) the inhibitor is a predetermined inhibitor previously characterized to inhibit NgR-p75 binding and to reduce axon growth inhibition mediated by NgR-p75 binding; (c) the inhibitor is selected from the group consisting of: an NgR peptide, a p75 peptide, an NgR peptide-specific antibody fragment and a p75 peptide-specific antibody fragment; and/or (d) the inhibitor is selected from the group consisting of (i) an NgR peptide which specifically inhibits NgR-p75 binding and does not inhibit NgR binding to MAG, OMgp and NogoA; (ii) a p75 peptide which specifically inhibits NgR-p75 binding and does not inhibit p75 binding to NGF and GT1b; (iii) an NgR peptide-specific antibody fragment which specifically inhibits NgR-p75 binding and does not inhibit NgR binding to MAG, OMgp and NogoA; and (iv) a p75 peptide-specific antibody fragment which specifically inhibits NgR-p75 binding and does not inhibit p75 binding to NGF and GT1b.

Kits for practicing the disclosed methods may also comprise printed or electronic instructions describing the applicable subject method.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

In one embodiment, the invention provides methods for assaying NgR-p75 binding, comprising the steps of (a) providing a mixture comprising a p75-binding NgR domain and an NgR-binding p75 domain; and (b) measuring a resultant binding of the NgR domain to the p75 domain as an indication of NgR-p75 binding.

The recited p75 is a well-studied mammalian neurotrophin receptor (e.g. Yamashita et al. (1999, Neuron 24, 585-93). p75 cDNA has been cloned from numerous, diverse species, including human (Genbank Accn No. XP 08138), mouse (Genbank Accn No. NP 150086), and rat (Genbank Accn No. P07174). p75 expression vectors are commercially available from numerous sources, e.g. Genzyme-Techne. NgR-binding domains of p75 are sufficient to effect specific NgR binding, and preferably competitively inhibit native p75 binding to NgR. As demonstrated below, NgR-binding p75 domains are readily defined from the extracellular domain of native p75, and NgR-binding is readily confirmed in routine, disclosed cell-based and cell-free binding assays. The NgR binding domain may be fused to additional peptide sequence, particularly additional p75 sequence. In particular embodiments, at least 50, preferably at least 100, more preferably at least 150, and most preferably all residues of the p75 extracellular domain may be used. If a transmembrane protein is compatible with the elected assay, native p75 may be used.

Similarly, the recited NgR is a well-studied mammalian neural axon protein which functions as a receptor for Nogo66 (e.g. Fournier et al., 2001, Nature 409, 341-4; Domeniconi et al., 2002, supra, and citations therein). NgR cDNA has been cloned from several species, including human (Genbank Accn No. BC011787), mouse (Genbank Accn No. NM-022982), and rat (Genbank Accn No. AY028438). NgR may be membrane-bound through a GPI linkage or cleaved therefrom. NgR may also be expressed recombinantly in suitable recombinant expression systems, wherein functional expression may be confirmed by the growth cone collapsing assays described herein. NgR expression vectors are commercially available from numerous sources. p75-binding domains of NgR are sufficient to effect specific binding to the extracellular domain of p75, and preferably competitively inhibit native NgR binding to p75. As demonstrated below, p75-binding NgR domains are readily defined from the native NgR, and p75-binding is readily confirmed in routine, disclosed cell-based and cell-free binding assays. As with the p75 component, the p75-binding domain of NgR may be fused to additional peptide sequence, particularly additional NgR sequence. In particular embodiments, at least 50, preferably at least 100, more preferably at least 150, and most preferably all residues of NgR may be used, preferably including all of the LRR, LRR-CT and CT domains (see, Fournier, et al., 2001, supra; WO01/51520). If a transmembrane protein is compatible with the elected assay, native membrane-bound, GPI-linked NgR may be used.

Where recited as isolated, the subject proteins are provided isolated from other components of their natural mileau, which may be effected by purification from such components or expression of the protein in a non-natural system. In particular embodiments, the isolated proteins are accompanied by other components which provide or interfere with or alter the axon growth inhibitory activity of the NgR-p75 binding. Preferred isolated proteins such as p75 and NgR are purified or recombinantly expressed, particularly on a surface of a cell.

A wide variety of assay formats may be used, some wherein (at least) one of the NgR domain and the p75 domain is soluble, wherein (at least) one of the NgR domain and the p75 domain is recombinantly expressed on the surface of a cell, wherein the mixture is cell-free, etc. Detailed protocols for implementing the recited steps are exemplified below and/or otherwise known in the art as guided by the present disclosure. For example, recited providing/contacting and measuring/detecting steps are tailored to the selected system. In vitro systems provide ready access to the recited mixture using routine laboratory methods, whereas in vivo systems, such as intact organisms or regions thereof, typically require surgical or pharmacological methods. More detailed such protocols are described below. Similarly, measuring and detecting steps are effected by evaluating different metrics, depending on the selected system. For in vitro binding assays, these include conventional solid-phase labeled protein binding assays, such as ELISA-type formats, solution-phase binding assays, such as fluorescent polarization or NMR-based assays, etc. For cell-based or in situ assays, metrics typically involve assays of axon growth as evaluated by linear measure, density, host mobility or other function improvement, etc.

In a preferred embodiment, the assay is used to screen for agents which modulate, particularly inhibit NgR-p75 binding. In these embodiments, the mixture further comprises an inhibitor of NgR-p75 binding, wherein but for the presence of the inhibitor, the mixture provides a control binding of the NgR domain to the p75 domain; and the measuring step measures an inhibitor-biased binding of the NgR domain to the p75 domain lower than the control binding. In a particular aspect, the inhibitor is a candidate inhibitor not previously characterized to bind NgR or p75, nor to inhibit NgR-p75 binding, nor to reduce axon growth inhibition mediated by NgR-p75 binding, and the measuring step characterizes the candidate inhibitor as reducing axon growth inhibition mediated by NgR-p75 binding. In particular screens, the inhibitor is selected from the group consisting of: an NgR peptide, a p75 peptide, an NgR peptide-specific antibody fragment and a p75 peptide-specific antibody fragment.

The screening assays may be used to detect both inhibitors and enhancers of NgR-p75 binding. Such enhancers provide reagents for inhibiting axon regeneration, useful in biomedical applications wherein regeneration is undesirable (e.g. neuromas; see, e.g. Xu et al., Brain Res 2002 Aug. 9; 946(1): 24-30). Accordingly, the invention also provides methods for characterizing an agent as modulating NgR-p75 binding, the method comprising the steps of (a) incubating a mixture comprising a p75-binding NgR domain, an NgR-binding p75 domain and an agent under conditions whereby but for the presence of the agent, the NgR domain and the p75 domain exhibit a control binding; and (b) detecting a resultant modulated binding of the NgR domain to the p75 domain different from the control binding as an indication that the agent modulates NgR-p75 binding.

The invention also provides specific inhibitors of NgR-p75 binding identified in the subject screens. Exemplary subject NgR-p75 binding inhibitors include NgR peptides which specifically inhibit NgR-p75 binding and do not inhibit NgR binding to MAG, OMgp and NogoA, particularly NgR CT domain peptides; p75 peptides which specifically inhibit NgR-p75 binding and do not inhibit p75 binding to NGF and GT1b, including both intracellular domain peptides and extracellular domain, non-ligand binding peptides; NgR peptide-specific antibody fragments which specifically inhibit NgR-p75 binding and do not inhibit NgR binding to MAG, OMgp and NogoA, particularly CT domain-targeting antibody fragments; and p75 peptide-specific antibody fragments which specifically inhibit NgR-p75 binding and do not inhibit p75 binding to NGF and GT1b, i.e. target non-ligand binding sites. In preferred examples, source antibodies of the subject NgR peptide-specific and p75 peptide-specific antibody fragments are monoclonal.

The invention also provides methods for reducing axon growth inhibition mediated by NgR-p75 binding and detecting resultant reduced axon growth inhibition, the methods comprising steps: contacting a mixture comprising an axon subject to NgR-p75 binding mediated growth inhibition with a specific, exogenous inhibitor of said NgR-p75 binding, under conditions wherein the inhibitor reduces said NgR-p75 binding mediated growth inhibition, and detecting a resultant reduced axon growth inhibition.

An NgR-p75 binding inhibitor exogenous to an axon or mixture comprising an axon is not naturally present with the axon or mixture. The recited axons are mammalian neuron axons, preferably adult neural axons, which may be peripheral or, preferably CNS neuron axons. As exemplified below, the methods may be applied to neural axons in vitro or in situ. By reducing axon growth inhibition in situ, the methods assist the repair of axons following injury or trauma, such as spinal cord injury. In addition, the methods, particularly as adapted to enhancers of NgR-p75 binding, may be applied to alleviate dysfunction of the nervous system due to hypertrophy of neurons or their axonal projections, such as occurs in diabetic neuropathy.

We have exemplified suitable inhibitors from diverse structures. Initial inhibitors were identified by selecting NgR-p75 binding inhibitors from natural sequence NgR and p75 peptides. These assays identified a number of specific NgR-p75 binding inhibitory peptides encompassing NgR CT sequences, including the exemplified species: hNR310/445, mNR310/445 and rNR310/445, as well as p75 sequences, including the exemplified species: hP001/250, rP001/251 and mP001/243. Additional protocols for producing and screening antagonistic peptides are found in GrandPre et al., Nature 2002 May 30; 417(6888):547-51, who report analogous, but functionally distinct, NgR peptides which promote axonal regeneration. Our natural NgR and p75 peptide sequences were subject to directed combinatorial mutation and binding analysis. Resultant synthetic-sequence peptides include the exemplified species: s1NR310/445, s2NR310/445, s3NR310/445, s1hP001/250, s1rP001/250 and s1mP001/243.

We also used a variety of NgR and p75 peptide immunogens to generate specific and binding-inhibitory antibodies and antibody fragments, including the exemplified monoclonal antibodies NP-H9838 and NP-H4620 and the exemplified fragments NPF-H2174 and NPF-H5819. Specific NgR-p75 binding inhibitors are also found in compound libraries, including the exemplified commercial fungal extract and a synthetic combinatorial organo-pharmacophore-biased libraries. Structural characterization of the exemplified p75 binding agents (XR-486573, XR-103739, XR-461994, SY-80564D, SY-25436I and SY-13947T) is effected by conventional organic analysis.

Of particular interest are size-minimized NgR CT peptides which effectively compete for p75 binding and size-minimized p75 extracellular domain peptides which effectively compete for NgR binding. By synthesizing and screening large libraries of such peptides for their ability to competitively inhibit NgR-p75 binding, and thereby reduce NgR-p75 binding-mediated axon growth inhibition, we identify numerous competitive binding peptides of varying length within a 136 amino acid region near the NgR C-terminus, exemplified with human, mouse and rat CT sequences (hNR310/445, SEQ ID NO:1; mNR310/445, SEQ ID NO:2; and rNR310/445, SEQ ID NO:3). Competitive peptides demonstrating >20% competitive activity compared with the source 136-mer are subject to combinatorial mutagenesis to generate synthetic peptide libraries from which we screen for even higher affinity binders. Preferred competitive peptides consist, or consist essentially of a size-minimized sequence within the disclosed human source 136-mer, preferably a sequence of fewer than 48, 38, 28 or 18 residues, wherein at least 6, 8, 12 or 16 residues are usually required for specific binding. Obtaining additional such native sequence and synthetic competitive peptides involves only routine peptide synthesis and screening in the disclosed binding and growth assays.

In particular applications, the target cells are injured mammalian neurons in situ, e.g. Schulz M K, et al., Exp Neurol. 1998 February; 149(2): 390-397; Guest J D, et al., J Neurosci Res. Dec. 1, 1997; 50(5): 888-905; Schwab M E, et al., Spinal Cord. 1997 July; 35(7): 469-473; Tatagiba M, et al., Neurosurg 1997 March; 40(3): 541-546; and Examples, below. For these in situ applications, compositions comprising the NgR-p75 binding inhibitors may be administered by any effective route compatible with therapeutic activity of the compositions and patient tolerance. For example, for CNS administration, a variety of techniques is available for promoting transfer of therapeutic agents across the blood brain barrier including disruption by surgery or injection, drugs which transiently open adhesion contact between CNS vasculature endothelial cells, and compounds which facilitate translocation through such cells. The compositions may also be amenable to direct injection or infusion, intraocular administration, or within/on implants e.g. fibers such as collagen fibers, in osmotic pumps, grafts comprising appropriately transformed cells, etc.

In a particular embodiment, the inhibitor is delivered locally and its distribution is restricted. For example, a particular method of administration involves coating, embedding or derivatizing fibers, such as collagen fibers, protein polymers, etc. with therapeutic agents, see also Otto et al. (1989) J Neurosci Res. 22, 83-91 and Otto and Unsicker (1990) J Neurosc 10, 1912-1921. The amount of binding inhibitor administered depends on the agent, formulation, route of administration, etc. and is generally empirically determined, and variations will necessarily occur depending on the target, the host, and the route of administration, etc.

The compositions may be advantageously used in conjunction with other neurogenic agents, neurotrophic factors, growth factors, anti-inflammatories, antibiotics etc.; and mixtures thereof, see e.g. *Goodman & Gilman's The Pharmacological Basis of Therapeutics*, 9$^{th}$ Ed., 1996, McGraw-Hill. Exemplary such other therapeutic agents include neuroactive agents such as in Table 1.

TABLE 1

Neuroactive agents which may be used in conjunction with NgR-p75 binding inhibitors.

| | | |
|---|---|---|
| NGF | Heregulin | Laminin |
| NT3 | IL-3 | Vitronectin |

TABLE 1-continued

| Neuroactive agents which may be used in conjunction with NgR-p75 binding inhibitors. | | |
|---|---|---|
| BDNF | IL-6 | Thrombospondin |
| NT4/5 | IL-7 | Merosin |
| CNTF | Neuregulin | Tenascin |
| GDNF | EGF | Fibronectin |
| HGF | TGFa | F-spondin |
| bFGF | TGFb1 | Netrin-1 |
| LIF | TGFb2 | Netrin-2 |
| IGF-I | PDGF BB | Semaphorin-III |
| IGF-II | PDGF AA | L1-Fc |
| Neurturin | BMP2 | NCAM-Fc |
| Percephin | BMP7/OP1 | KAL-1 |

Abbreviations:
NGF, nerve growth factor;
NT, neurotrophin;
BDNF, brain-derived neurotrophic factor;
CNTF, ciliary neurotrophic factor;
GDNF, glial-derived neurotrophic factor;
HGF, hepatocyte growth factor;
FGF, fibroblast growth factor;
LIF, leukemia inhibitory factor;
IGF, insulin-like growth factor;
IL, interleukin;
EGF, epidermal growth factor;
TGF, transforming growth factor;
PDGF, platelet-derived growth factor;
BMP, bone morphogenic protein;
NCAM, neural cell adhesion molecule.

In particular embodiments, the NgR-p75 binding inhibitor is administered in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. As such the compositions, in pharmaceutically acceptable dosage units or in bulk, may be incorporated into a wide variety of containers, which may be appropriately labeled with a disclosed use application. Dosage units may be included in a variety of containers including capsules, pills, etc.

The invention also provides compositions and mixtures specifically tailored for practicing the subject methods. For example, an in vitro mixture for use in the subject binding assays comprises premeasured, discrete and contained amounts of NgR, p75 and an agent, wherein at least one of the NgR and p75 is soluble and GPI-cleaved. Kits for practicing the disclosed methods may also comprises printed or electronic instructions describing the applicable subject method.

EXAMPLES

In inhibiting neurite outgrowth, multiple myelin components, including the extracellular domain of Nogo-A (Nogo-66) (Fournier, et al., 2001, supra), OMgp (Wang, et al. 2002, supra), and MAG (Liu, et al. Science Jun. 27, 2002; [epub ahead of print]; Domeniconi et al., 2002, supra), have been recently shown to act through the same Nogo receptor (NgR). We demonstrate here that p75 specifically and directly interacts with NgR, and transduces inhibitory ligand-binding signals. While a recombinant protein harboring the extracellular domain of p75 neutralized the inhibitory activity of myelin components, the neurons derived from P75 knockout mice are no longer responsive to each of these myelin inhibitors. We show that repressing p75 and its downstream signaling helps lesioned axons overcome inhibitory activity associated with CNS myelin.

When we overexpress HA-tagged P75 and FLAG-tagged NgR into CHO cells, we find that p75 can be co-immunoprecipitated with NgR, but not with a control transmembrane protein Plexin A3. We also utilize a cell surface binding assay to better visualize the NgR/P75 interaction. An alkaline phosphatase (AP) fusion protein containing the extracellular domain of P75 (AP-p75), but not AP protein alone, is able to bind CHO cells expressing full-length NgR specifically. This binding of AP-75 to NgR-expressing cells is substantiated by addition of MAG-Fc, indicating that MAG is able to induce the formation of P75/NgR complex. Although P75 has been previously reported to affect the binding of neurotrophins to Trk receptors (Bibel, et al. EMBO J 18, 616-622, 1999) and to form a MAG receptor complex with GT1b (Yamashita, et al., 2002, supra), we find that P75 expression does not enhance the MAG binding of NgR-expressing cells. We obtain comparable results with OMgp and Nogo ligands. Our data indicate that P75 and NgR form receptor complexes in a ligand-dependent manner.

We also determined the structural basis of the interaction between P75 and NgR. AP-75 lacking the transmembrane and intracellular domains of P75 is able to bind to full-length NgR, indicating that the interaction of P75 with NgR is mediated through its extracellular domain. The amino-terminal region covering eight leucine rich repeats (LRR) and the LRR C-terminal domain (LRRCT) has been shown to be sufficient to interact with MAG, OMgp and Nogo-66. Furthermore, a truncated NgR lacking the unique carboxyl-terminal region (CT) is able to neutralize the inhibitory activity of MAG, OMgp and Nogo ligands, and both the N-terminal LRR and LRRCT and the C-terminal CT domains are indispensable for interacting with P75.

We use a neurite outgrowth assay to compare the responses of neurons from wild type mice and those carrying a mutation in the P75 gene to individual inhibitors (Lee et al., Cell 1992 May 29; 69(5):737-49). Neurite outgrowth of DRG neurons from P75 (−/−) was not inhibited by MAG-Fc. Similarly, although both GST-66 and OM-his efficiently inhibited the neurite outgrowth from wild type neurons, neither of these proteins restrict neurite outgrowth from P75 (−/−) mice, indicating that P75 is required for the inhibitory activity of these myelin inhibitors.

Reagents that block or accelerate p75-NgR interactions affect the neurite outgrowth responses to inhibitors. For example, a Fc fusion protein harboring the extracellular domain (amino acids 1 to 250) of P75 (P75-Fc) blocks the inhibitory activity of each myelin inhibitors in a dose-dependent manner. Similarly, P75-Fc also efficiently abolishes the activity of Nogo-66 and OMgp proteins in inducing growth cone collapse of E13 chick dorsal root ganglion neurons (E13 DRG).

In addition, antibodies against the extracellular domain of P75 (1554), but not control antibodies, could specifically enhance the binding of AP-75 to NgR-expressing cells both in the presence and in the absence of MAG-Fc ligand. These anti-P75 antibodies enhance significantly the inhibitory activity of myelin proteins. We made recombinant retroviruses expressing a truncated NgR which possessed the ability to bind to all of the inhibitory ligands, but not to P75. Upon expression in cerebellar granule neurons (CGNs), this truncated NgR, but not full-length NgR, blocks the inhibitory responses elicited by immobilized inhibitors. These results demonstrate that the extracellular domain of P75 mediates the inhibitory signals through its interaction with NgR.

We utilize recombinant lentivirus-mediated gene expression to express a full-length or truncated P75 lacking the intracellular domain in P7-9 CGNs. While full-length p75 does not change the responsiveness of infected neurons to myelin inhibitors, the truncated p75 allows robust neurite outgrowth on each of these inhibitory substrates. These results indicate that the intracellular domain of P75 is required for mediating myelin associated inhibitory activities.

The expressions of P75 and NgR overlap throughout CNS at E13 and P13. However, although NgR expression persists, P75 expression declines in the adult CNS. However, a spinal cord hemisection lesion in adult rats dramatically induces the expression of P75 in the axonal fibers around the injury site. P75 induction is detected at 3 days post-injury, but is most prominent at 1-2 week post-injury. We use p75-NgR binding inhibitors in this system to show that interfering with P75 signaling after CNS axonal injury alleviates myelin-dependent inhibition of axonal regeneration.

We use p75 promoter-luciferase reporter constructs to identify regulators of p75 transcriptional expression, including GC element binding peptides (e.g. Poukka et al. Biochem Biophys Res Commun 1996 Dec. 13; 229(2):565-70). Using the rat spinal cord hemisection lesion system (supra), we use inhibitors of p75 expression to show that suppressing the injury-induced P75 upregulation after CNS axonal injury alleviates myelin-dependent inhibition of axonal regeneration.

We screened a variety of candidate agents for NgR-p75 binding inhibition using several assay protocols. The selected binding assay formats are guided by structural requirements of the candidate agents and include COS-expression, solid phase ELISA-type assays, and fluorescent polarization assays. Our preferred assay uses AP fused to an NgR-binding domain of p75 to directly assay NgR-p75 binding inhibition. Candidate agents are selected from natural and synthetic peptide libraries biased to natural NgR CT and natural p75 extracellular domain sequences, p75- and NgR-specific monoclonal antibody (Mab) and Mab fragment libraries, a commercial fungal extract library, and a synthetic combinatorial organo-pharmacophore-biased library. Of several hundred binding inhibitors, selected exemplary inhibitors subject to in vitro growth cone collapse and in vivo axon regeneration activity assays (below) are shown in Table 2.

TABLE 2

Exemplary NgR-p75 binding inhibitors subject to in vitro growth cone collapse and in vivo axon regeneration activity assays; (u), structure not yet determined.

| Inhibitor | Class/Source | Sequence/ Structure | Binding Inhibition |
|---|---|---|---|
| 1. hNR310/445 | natural peptide | SEQ ID NO: 1 | +++ |
| 2. mNR310/445 | natural peptide | SEQ ID NO: 2 | +++ |
| 3. rNR310/445 | natural peptide | SEQ ID NO: 3 | +++ |
| 4. s1NR310/445 | synthetic peptide | SEQ ID NO: 4 | +++ |
| 5. s2NR310/445 | synthetic peptide | SEQ ID NO: 5 | +++ |
| 6. s3NR310/445 | synthetic peptide | SEQ ID NO: 6 | +++ |
| 7. hP001/250 | natural peptide | SEQ ID NO: 7 | +++ |
| 8. rP001/251 | natural peptide | SEQ ID NO: 8 | +++ |
| 9. mP001/243 | natural peptide | SEQ ID NO: 9 | +++ |
| 10. s1hP001/250 | synthetic peptide | SEQ ID NO: 10 | +++ |
| 11. s1rP001/250 | synthetic peptide | SEQ ID NO: 11 | +++ |
| 12. s1mP001/243 | synthetic peptide | SEQ ID NO: 12 | +++ |
| 13. NP-H9838 | p74-specific Mab | IgG | +++ |
| 14. NP-H4620 | NgR-specific Mab | IgG | +++ |
| 15. NPF-H2174 | Fab fragment (Mab) | IgG Fab2 | +++ |
| 16. NPF-H5819 | Fab fragment (Mab) | IgG Fab2 | +++ |
| 17. XR-486573 | fungal extract cmpd | natural (u) | +++ |
| 18. XR-103739 | fungal extract cmpd | natural (u) | +++ |
| 19. XR-461994 | fungal extract cmpd | natural (u) | +++ |
| 20. SY-80564D | combinatorial cmpd | synthetic (u) | +++ |
| 21. SY-25436I | combinatorial cmpd | synthetic (u) | +++ |
| 22. SY-13947T | combinatorial cmpd | synthetic (u) | +++ |

Corticospinal Tract (CST) Regeneration Assay. NgR-p75 binding inhibitors demonstrating inhibition of NgR-p75 binding-mediated in vitro axon growth cone collapse are assayed for their ability to improve corticospinal tract (CST) regeneration following thoracic spinal cord injury by promoting CST regeneration into human Schwann cell grafts in the methods of Guest et al. (1997, supra). For these data, the human grafts are placed to span a midthoracic spinal cord transection in the adult nude rat, a xenograft tolerant strain. Inhibitors determined to be effective in in vitro collapse assays are incorporated into a fibrin glue and placed in the same region. Anterograde tracing from the motor cortex using the dextran amine tracers, Fluororuby (FR) and biotinylated dextran amine (BDA), are performed. Thirty-five days after grafting, the CST response is evaluated qualitatively by looking for regenerated CST fibers in or beyond grafts and quantitatively by constructing camera lucida composites to determine the sprouting index (SI), the position of the maximum termination density (MTD) rostral to the GFAP-defined host/graft interface, and the longitudinal spread (LS) of bulbous end terminals. The latter two measures provide information about axonal die-back. In control animals (graft only), the CST do not enter the SC graft and undergo axonal die-back. As shown in Table 3, the exemplified inhibitors dramatically reduce axonal die-back and cause sprouting, and these in vivo data are consistent with the corresponding growth cone collapsing activity.

TABLE 3

In vitro and in vivo neuronal regeneration with exemplary NgR-p75 binding inhibitors.

| Inhibitor | Collapse Inhibition | Reduced Die-Back | Promote Sprouting |
|---|---|---|---|
| 1. hNR310/445 | ++++ | ++++ | ++++ |
| 2. mNR310/445 | ++++ | ++++ | ++++ |
| 3. rNR310/445 | +++ | +++ | +++ |
| 4. s1NR310/445 | ++++ | ++++ | ++++ |
| 5. s2NR310/445 | +++ | +++ | +++ |
| 6. s3NR310/445 | ++++ | ++++ | ++++ |
| 7. hP001/250 | ++++ | ++++ | ++++ |
| 8. rP001/251 | +++ | +++ | +++ |
| 9. mP001/243 | +++ | +++ | +++ |
| 10. s1hP001/250 | +++ | +++ | +++ |
| 11. s1rP001/250 | +++ | +++ | +++ |
| 12. s1mP001/243 | ++++ | ++++ | ++++ |
| 13. NP-H9838 | ++++ | ++++ | ++++ |
| 14. NP-H4620 | ++++ | ++++ | ++++ |
| 15. NPF-H2174 | +++ | +++ | +++ |
| 16. NPF-H5819 | +++ | +++ | +++ |
| 17. XR-486573 | +++ | +++ | +++ |
| 18. XR-103739 | ++++ | ++++ | ++++ |
| 19. XR-461994 | ++++ | ++++ | ++++ |
| 20. SY-80564D | +++ | +++ | +++ |
| 21. SY-25436I | ++++ | ++++ | ++++ |
| 22. SY-13947T | +++ | +++ | +++ |

Peripheral Nerve Regeneration Assay. NgR-p75 binding inhibitors demonstrating inhibition of NgR-p75 binding-mediated in vitro axon growth cone collapse as described above are also incorporated in the implantable devices described in U.S. Pat. No. 5,656,605 and tested for the promotion of in vivo regeneration of peripheral nerves. Prior to surgery, 18 mm surgical-grade silicon rubber tubes (I.D. 1.5 mm) are prepared with or without guiding filaments (four 10-0 monofilament nylon) and filled with test compositions comprising the inhibitors of Table 2. Experimental groups consist of: 1. Guiding tubes plus Biomatrix 1™ (Biomedical Technologies, Inc., Stoughton, Mass.); 2. Guiding tubes plus Biomatrix plus filaments; 3-24. Guiding tubes plus Biomatrix 1™ plus inhibitors The sciatic nerves of rats are sharply transected at mid-thigh and guide tubes containing the test substances with and without guiding filaments sutured over distances of approximately 2 mm to the end of the nerves. In each experiment, the other end of the guide tube is left open. This model simulates a severe nerve injury in which no contact with the distal end of the nerve is present. After four weeks, the distance of regeneration of axons within the guide tube is tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve is preserved with a fixative. Cross sections are prepared at a point approximately 7 mm from the transection site. The diameter of the regenerated nerve and the number of myelinated axons observable at this point are used as parameters for comparison.

Measurements of the distance of nerve regeneration document therapeutic efficacy. Similarly, plots of the diameter of the regenerated nerve measured at a distance of 7 mm into the guide tube as a function of the presence or absence of one or more inhibitors demonstrate a similar therapeutic effect of all 22 tested. No detectable nerve growth is measured at the point sampled in the guide tube with the matrix-forming material alone. The presence of guiding filaments plus the matrix-forming material (no inhibitors) induces only very minimal regeneration at the 7 mm measurement point, whereas dramatic results, as assessed by the diameter of the regenerating nerve, are produced by the device which consisted of the guide tube, guiding filaments and binding inhibitor compositions. Finally, treatments using guide tubes comprising either a matrix-forming material alone, or a matrix-forming material in the presence of guiding filaments, result in no measured growth of myelinated axons. In contrast, treatments using a device comprising guide tubes, guiding filaments, and matrix containing inhibitor compositions consistently result in axon regeneration, with the measured number of axons being increased markedly by the presence of guiding filaments.

NgR-p75 Binding Inhibitory Monoclonal Antibodies Promote Axon Regeneration In Vivo. In these experiments, our NP-H9838 and NP-H4620 monoclonal antibodies are shown to promote axonal regeneration in the rat spinal cord. Tumors producing our NgR-p75 binding inhibitory antibodies, implantation protocols and experimental design are substantially as used for IN-1 as described in Schnell et al., Nature 1990 Jan. 18; 343(6255):269-72. In brief, our monoclonal antibodies are applied intracerebrally to young rats by implanting antibody-producing tumours. In 2-6-week-old rats we make complete transections of the corticospinal tract, a major fibre tract of the spinal cord, the axons of which originate in the motor and sensory neocortex. Previous studies have shown a complete absence of cortico-spinal tract regeneration after the first postnatal week in rats, and in adult hamsters and cats. In our treated rats, significant sprouting occurs at the lesion site, and fine axons and fascicles can be observed up to 7-11 mm caudal to the lesion within 2-3 weeks. In control rats, a similar sprouting reaction occurs, but the maximal distance of elongation rarely exceeds 1 mm. These results demonstrate the capacity for CNS axons to regenerate and elongate within differentiated CNS tissue after neutralization of axon growth inhibition.

NgR-p75 Binding Inhibitory Monoclonal Antibody Fragments Promote Axon Regeneration in Vivo. In these experiments, our NgR-p75-binding inhibitory monoclonal antibody fragments are shown to promote sprouting of Purkinje cell axons. Experimental protocols were adapted from Buffo et al., 2000, J Neuroscience 20, 2275-2286.

Animals and surgical procedures. Adult Wistar rats (Charles River, Calco, Italy) are deeply anesthetized by means of intraperitoneal administration of a mixture of ketamine (100 mg/kg, Ketalar; Bayer, Leverkusen, Germany) and xylazine (5 mg/kg, Rompun; Bayer).

Fab fragment or antibody injections are performed as previously described (Zagrebelsky et al., J Neurosci. 1998 Oct. 1; 18(19):7912-29). Animals are placed in a stereotaxic apparatus, and the dorsal cerebellar vermis exposed by drilling a small hole on the posterosuperior aspect of the occipital bone. The meninges are left intact except for the small hole produced by the injection pipette penetration. In test rats recombinant Fab fragments of the NP-H9838 and NP-H4620 antibodies (produced in *E. coli*), which neutralizes NgR-p75 binding-associated axon growth cone collapse in vitro, are injected into the cerebellar parenchyma. Three 1 μl injections of Fab fragments in saline solution (5 mg/ml) are performed 0.5-1 mm deep along the cerebellar midline into the dorsal vermis (lobules V-VII). The injections are made by means of a glass micropipette connected to a PV800 Pneumatic Picopump (WPI, New Haven, Conn.). The frequency and duration of pressure pulses are adjusted to inject 1 μl of the solution during a period of ~10 min. The pipette is left in situ for 5 additional minutes to avoid an excessive leakage of the injected solution. As a control, an affinity-purified $F(ab')_2$ fragment of a mouse anti-human IgG (Jackson ImmunoResearch Laboratories, West Grove, Pa.) is applied to another set of control rats using the same procedure. Survival times for these two experimental sets are 2, 5, 7 and 30 d (four animals for each time point). An additional set of intact animals is examined as untreated controls.

Histological procedures. At different survival times after surgery, under deep general anesthesia (as above), the rats are transcardially perfused with 1 ml of 4% paraformaldehyde in 0.12 M phosphate buffer, pH 7.2-7.4. The brains are immediately dissected, stored overnight in the same fixative at 4° C., and finally transferred in 30% sucrose in 0.12 M phosphate buffer at 4° C. until they sink. The cerebella are cut using a freezing microtome in several series of 30-μm-thick sagittal sections. One series is processed for NADPH diaphorase histochemistry. These sections are incubated for 3-4 hr in darkness at 37° C. in a solution composed of -NADPH (1 mg/ml, Sigma, St. Louis, Mo.) and nitroblue tetrazolium (0.2 mg/ml, Sigma) in 0.12 M phosphate buffer with 0.25% Triton X-100. In some cases (two animals per treated and control sets at 2 and 5 d survival), microglia are stained by incubating one section series with biotinylated *Griffonia simplicifolia* isolectin B4 [1:100 in phosphate buffer with 0.25% Triton X-100; Sigma] overnight at 4° C. Sections are subsequently incubated for 30 min in the avidin-biotin-peroxidase complex (Vectastain, ABC Elite kit, Vector, Burlingame, Calif.) and revealed using the 3,3'diaminobenzidine (0.03% in Tris HCl) as a chromogen.

All of the other series are first incubated in 0.3% $H_2O_2$ in PBS to quench endogenous peroxidase. Then, they are incubated for 30 min at room temperature and overnight at 4° C. with different primary antibodies: anti-calbindin D-28K (monoclonal, 1:5000, Swant, Bellinzona, Switzerland), to visualize Purkinje cells; anti-c-Jun (polyclonal, 1:1000, Santa Cruz Biotechnology, Santa Cruz, Calif.); and anti-CD11b/c (monoclonal OX-42, 1:2000, Cedarlane Laboratories, Hornby, Ontario) to stain microglia. All of the antibodies are diluted in PBS with 0.25% Triton X-100 added with either normal horse serum or normal goat serum depending on the species of the second antibody. Immunohistochemical staining is performed according to the avidin-biotin-peroxidase method (Vectastain, ABC Elite kit, Vector) and revealed using the 3,3'diaminobenzidine (0.03% in Tris HCl) as a chromogen. The reacted sections are mounted on chrome-alum gelatinized slides, air-dried, dehydrated, and coverslipped.

Quantitative analysis. Quantification of reactive Purkinje cells in the different experiments is made by estimating the neurons labeled by c-Jun antibodies as previously described (Zagrebelsky et al., 1998, supra). For each animal, three immunolabeled sections are chosen. Only vermal sections close to the cerebellar midline that contain the injection sites are considered. The outline of the selected sections is reproduced using the Neurolucida software (MicroBrightField, Colchester, Vt.) connected to an E-800 Nikon microscope, and the position of every single-labeled cell carefully marked. The number of labeled cells present in the three reproduced sections is averaged to calculate values for every individual animal, which are used for statistical analysis carried out by Student's t test.

A morphometric analysis of Purkinje axons in the different experimental conditions for each animal, is performed using three anti-calbindin-immunolabeled sections, contiguous to those examined for c-Jun, as described in Buffo et al. (supra). Morphometric measurements are made on 200×250 μm areas of the granular layer chosen by superimposing a grid of this size on the section. The selected areas encompass most of the granular layer depth and contain only minimal portions of Purkinje cell layer or axial white matter. In each of the selected sections is sampled one area from the dorsal cortical lobules and one from the ventral cortical lobules. In addition, to sample from the different parts of these two cortical regions, areas from different lobules are selected in the three sections belonging to each individual animal, one area in each of lobules V, VI, and VII and one in lobules I, II, and IX. All of the anti-calbindin-immunolabeled Purkinje axon segments contained within the selected areas are reproduced using the Neurolucida software (MicroBrightField) connected to an E-800 Nikon microscope with 20× objective, corresponding to 750× magnification on the computer screen. Each labeled axon segment or branch is reproduced as a single profile. From these reproductions the software calculates the number of axon profiles, their individual length, and the total length of all the reproduced segments, the mean profile length (total length/number of profiles), and the number of times that the axons crossed a 25×25 μm grid superimposed on the selected area. Data calculated from the different areas in the three sections sampled from each cerebellum are averaged to obtain values for every individual animal. Statistical analysis is performed on the latter values (n=4 for all groups at all time points) by Student's t test and paired t test.

Our results reveal significant promotion of sprouting of Purkinje cell axons in test rats subject to NgR-p75 binding inhibitory monoclonal antibody fragments as compared with the control animals.

Exemplary experimental protocols: Binding experiments: Sequence encoding the extracellular domain of rat p75 was subcloned into the expression vector AP-5 to express an AP-p75 fusion protein tagged with both a polyhistidine and a myc epitope. The resultant plasmid DNA was transfected into COS-7 cells and the secreted protein purified using nickel-Agarose resins (Qiagen). Cell surface binding with AP-p75 and other AP proteins were performed as described previously. For visualization of bound proteins, NBT and BCIP were used as AP substrates.

Generation of recombinant proteins and viruses and Co-precipitation: In co-precipitation experiments, 2 ug GST or GST-NgR were first immobilized to glutathione-Agarose beads and the beads were further incubated with or without 1 μg OM-his in the presence of 2 ug of AP or AP-66 at 4° C. for 2 hr. After extensive washing, bound proteins were resolved with SDS-PAGE and detected by Western blotting.

Neurite outgrowth and growth cone collapse assays: Briefly, P7-9 rat or mouse CGNs were dissected and then plated at a density of $1\times10^5$ cells per well. Cells were cultured for 24 hr prior to fixation with 4% paraformaldehyde and staining with a neuronal specific anti-B-tubulin antibody (TuJ-1, Covance). Neurite lengths were measured from at least 150 CGNs per condition, from duplicate wells per experiment, and from three independent experiments and quantified.

Chick E13 DRG explants cultured overnight were used for growth cone collapse assays. In untreated control cultures, 80-85% of the growth cones were intact. To assess the effects of PI-PLC treatment, cultures were pre-incubated with 2 U/ml PI-PLC for 30 min prior to treatment with individual test proteins for an additional 30 min. To express NgR in E7 retinal ganglion neurons, we infected the explants with recombinant HSV for 24 hr. After incubation with each test protein for 30 min, retinal explants were fixed in 4% paraformaldehyde and 15% sucrose. Infection of HSV-LacZ was detected by a standard B-galactosidase staining protocol. FLAG-NgR expression was detected by incubating paraformaldehyde-fixed cultures with M2 anti-FLAG antibody. Bound antibody was detected by incubation with AP-conjugated anti-rabbit IgG secondary antibody and reaction with NBT and BCIP. Growth cone collapse was quantified only in those positively stained for B-galactosidase or immunoreactive for the FLAG epitope.

RELEVANT REFERENCES

Schwab, M. E., and Bartholdi, D. Degeneration and regeneration of axons in the lesioned spinal cord. *Physiol. Rev.* 76, 319-370 (1996).

Horner, P. J,. Gage, F. H. Regenerating the damaged central nervous system. *Nature* 407, 963-970 (2000).

McKerracher, L et al., Identification of myelin-associated glycoprotein as a major myelin-derived inhibitor of neurite growth. *Neuron* 13, 805-811 (1994).

Mukhopadhyay, G. et al., A novel role for myelin-associated glycoprotein as an inhibitor of axonal regeneration. *Neuron* 13, 757-767 (1994).

Chen, M. S. et al., Nogo-A is a myelin-associated neurite outgrowth inhibitor and an antigen for monoclonal antibody IN-1. *Nature* 403, 434-439 (2000).

GrandPre, T., Nakamura, F., Vartanian, T., Strittmatter, S. M. Identification of the Nogo inhibitor of axon regeneration as a Reticulon protein. *Nature* 403, 439-444 (2000).

Prinjha, R. et al., Inhibitor of neurite outgrowth in humans. *Nature* 403, 383-384 (2000).

Tessier-Lavigne, M, Goodman, C. S. Perspectives: neurobiology. Regeneration in the Nogo zone. *Science* 287, 813-814 (2000).

Luo, Y., Raible, D., Raper, J. A. Collapsin: a protein in brain that induces the collapse and paralysis of neuronal growth cones. *Cell* 75, 217-227 (1993).

Mikol, D. D., Stefansson, K. A phosphatidylinositol-linked peanut agglutinin-binding glycoprotein in central nervous system myelin and on oligodendrocytes. *J Cell Biol* 106, 1273-1279 (1988).

Mikol, et al. The oligodendrocyte-myelin glycoprotein belongs to a distinct family of proteins and contains the HNK-1 carbohydrate. *J Cell Biol* 110, 471-479 (1990).

He, Z., and Tessier-Lavigne, M. Neuropilin is a receptor for the axonal chemorepellent Semaphorin III. *Cell* 90, 739-751, 1997.

Habib, et al. Expression of the oligodendrocyte-myelin glycoprotein by neurons in the mouse central nervous system. *J Neurochem* 70, 1704-1711 (1998).

Niederost, et al. Bovine CNS myelin contains neurite growth-inhibitory activity associated with chondroitin sulfate proteoglycans. *J Neurosci* 19, 8979-8989 (1999).

Spillmann, et al. Identification and characterization of a bovine neurite growth inhibitor (bNI-220). *J Biol Chem* 273, 19283-19293 (1998).

Flanagan, et al. Alkaline phosphatase fusion proteins for molecular characterization and cloning of receptors and their ligands. *Methods Enzymol* 327, 198-210 (2000).

Liu B. P, Strittmatter S. M. Semaphorin-mediated axonal guidance via Rho-related G proteins. *Curr Opin Cell Biol* 13, 619-626 (2001).

Norton, W. T., and Poduslo, S. E. Myelination in rat brain: method of myelin isolation. *J. Neurochem*. 21, 749-757 (1973).

Neve, R. L, Howe, J. R, Hong, S, Kalb, R. G. Introduction of the glutamate receptor subunit 1 into motor neurons in vitro and in vivo using recombinant herpes simplex virus. *Neuroscience* 79, 435-447 (1997).

Huang, et al. A therapeutic vaccine approach to stimulate axon regeneration in the adult mammalian spinal cord. *Neuron* 24, 639-647 (1999).

Cohen-Cory, S. and Fraser, S. E. Effects of brain-derived neurotrophic factor on optic axon branching and remodeling in vivo. *Nature* 378, 192-196 (1995).

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for assaying Nogo receptor (NgR)-neurotrophin receptor p75NTR (p75) binding, the method comprising the steps of:

providing a mixture comprising a p75-binding NgR domain and an NgR-binding p75 domain; and directly measuring binding of the NgR domain to the p75 domain as an indication of the assayed NgR-p75 binding.

2. A method according to claim 1, wherein binding of the NgR domain to the p75 domain is measured in the presence of an inhibitor of NgR-p75 binding and compared to a control amount of binding in the absence of the inhibitor, and wherein binding in the presence of the inhibitor is lower than the control binding.

3. A method according to claim 2, wherein the inhibitor is selected from the group consisting of: an NgR peptide, a p75 peptide, an NgR peptide-specific antibody fragment and a p75 peptide-specific antibody fragment.

4. A method according to claim 1, wherein one of the NgR domain and the p75 domain is soluble.

5. A method according to claim 1, wherein one of the NgR domain and the p75 domain is expressed on the surface of a cell.

6. A method according to claim 1, wherein the mixture is cell-free.

7. A method according to claim 1, wherein the mixture comprises an NgR comprising the NgR domain, and a p75 extracellular domain comprising the p75-domain.

8. A method according to claim 1, wherein one of the NgR domain and p75 domain is soluble and the other is expressed on the surface of a cell.

9. A method according to claim 1 wherein the measuring step is a co-immunoprecipitation assay, a solid phase ELISA-type assay, or a fluorescent polarization assay.

10. A method for characterizing an agent as modulating Nogo receptor (NgR)-neurotrophin receptor p75NTR (p75) binding, the method comprising the steps of:

A) incubating a mixture comprising a p75-binding NgR domain and an NgR-binding p75 domain under conditions that allow for binding between the two domains and directly measuring the degree of binding between the two domains, and B) incubating a mixture comprising a p75-binding NgR domain, an NgR-binding p75 domain, and an agent under the same conditions as in A), and directly measuring the degree of binding between the two domains;

wherein a difference between the binding measured in A) and the binding measured in B) indicates that the agent modulates NgR-p75 binding.

11. A method according to claim 10, wherein one of the NgR domain and the p75 domain is soluble.

12. A method according to claim 10, wherein one of the NgR domain and the p75 domain is recombinantly expressed on the surface of a cell.

13. A method according to claim 10, wherein the mixture is cell-free.

14. A method according to claim 10, wherein the mixture comprises an NgR comprising the NgR domain, and a p75 extracellular domain comprising the p75-domain.

15. A method according to claim 10, wherein one of the NgR domain and p75 domain is soluble and the other is expressed on the surface of a cell.

16. A method according to claim 10 wherein the detecting step is a co-immunoprecipitation assay, a solid phase ELISA-type assay, or a fluorescent polarization assay.

17. A method for assaying Nogo receptor (NgR)-neurotrophin receptor p75NTR (p75) binding, the method comprising the steps of:

recombinantly expressing a p75-binding NgR domain and an NgR-binding p75 domain; and measuring binding of the NgR domain to the p75 domain.

18. A method according to claim 17, wherein binding of the NgR domain to the p75 domain is measured in the presence of an inhibitor of NgR-p75 binding and compared to a control amount of binding in the absence of the inhibitor, and wherein binding in the presence of the inhibitor is lower than the control binding.

19. A method according to claim 17, wherein one of the NgR domain and the p75 domain is soluble.

20. A method according to claim 17, wherein one of the NgR domain and the p75 domain is expressed on the surface of a cell.

21. A method according to claim 17, wherein the mixture is cell-free.

* * * * *